United States Patent [19]

Plessers et al.

[11] Patent Number: 4,998,432
[45] Date of Patent: Mar. 12, 1991

[54] APPARATUS AND METHOD FOR MEASURING A GAS CONTENT OF LIQUID METAL AND PROBE USED THEREIN

[75] Inventors: Jacques J. Plessers, Houthalen; Rudi Maes, Zonhoven, both of Belgium

[73] Assignee: Electro-Nite International N.V., Antwerp, Belgium

[21] Appl. No.: 283,998

[22] PCT Filed: Mar. 16, 1988

[86] PCT No.: PCT/EP88/00206

§ 371 Date: Nov. 17, 1988

§ 102(e) Date: Nov. 17, 1988

[87] PCT Pub. No.: WO88/07197

PCT Pub. Date: Sep. 22, 1988

[30] Foreign Application Priority Data

Mar. 18, 1987 [BE] Belgium ............................. 08700279
Feb. 10, 1988 [BE] Belgium ............................. 08800152
Feb. 10, 1988 [BE] Belgium ............................. 08800154

[51] Int. Cl.⁵ ........................ G01N 7/14; G01N 27/18
[52] U.S. Cl. ............................................... 73/19.07
[58] Field of Search ............................................ 73/19

[56] References Cited

U.S. PATENT DOCUMENTS

| | | | |
|---|---|---|---|
| 2,861,450 | 11/1958 | Ransley | 73/19 |
| 4,116,475 | 9/1978 | Glaser et al. | 285/133 R |
| 4,454,748 | 6/1984 | Terai et al. | 73/19 |
| 4,624,128 | 11/1986 | Pelton | 73/19 |
| 4,731,732 | 3/1989 | Warchd et al. | 73/19 X |
| 4,757,707 | 7/1988 | Harvey et al. | 73/19 |
| 4,907,440 | 3/1990 | Martin et al. | 79/19.07 |

FOREIGN PATENT DOCUMENTS

| | | |
|---|---|---|
| 898319 | 5/1984 | Belgium . |
| 0212371 | 4/1987 | European Pat. Off. . |
| 2123957 | 2/1984 | United Kingdom . |

Primary Examiner—John Chapman
Assistant Examiner—Joseph W. Roskos
Attorney, Agent, or Firm—Panitch Schwarze Jacobs & Nadel

[57] ABSTRACT

A probe for immersion in a bath of liquid metal includes a gas supply pipe closed at its lower end by a stopper which melts in liquid metal, a gas collecting portion having a diaphragm which allows gas to pass but retains liquid metal for collecting the gas bubbling from the supply pipe through the metal, and a gas discharge pipe connected to the gas collecting portion. A gas circuit has one end connected to the gas supply pipe and another end connected to the gas discharge pipe. The circuit includes a gas detector and a pump mounted therein for moving the gas through the circuit. A lance through which the gas circuit extends, includes one portion of a two portion quick-acting coupling and the probe includes the other portion of the coupling. The gas is dried as it circulates in the circuit.

47 Claims, 5 Drawing Sheets

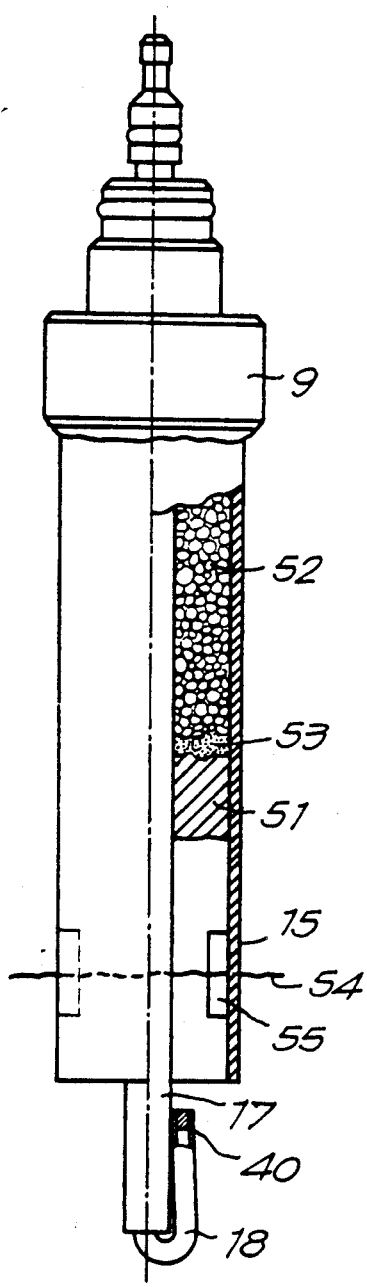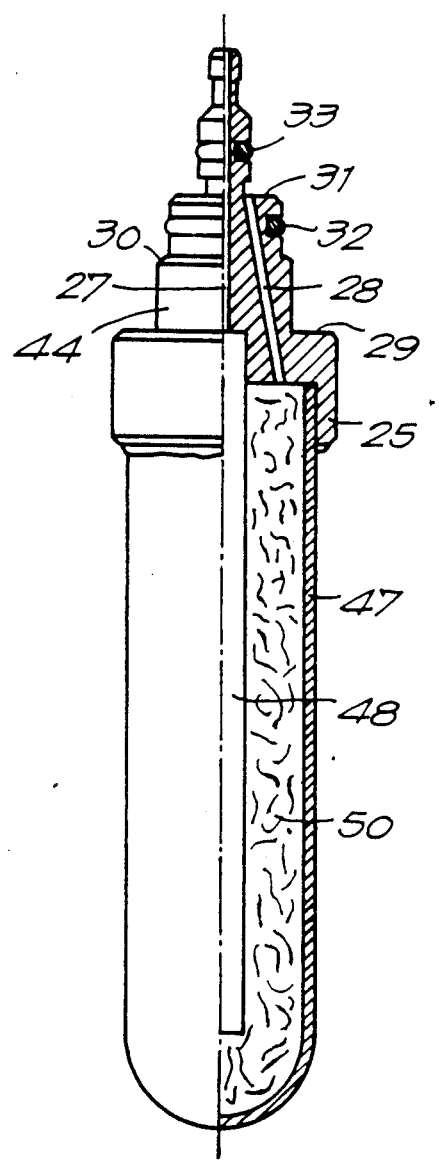

APPARATUS AND METHOD FOR MEASURING A GAS CONTENT OF LIQUID METAL AND PROBE USED THEREIN

The invention relates to an apparatus for measuring a gas content of liquid metal, which apparatus contains a probe which is designed to be immersed in the liquid metal and which has in its turn a gas supply line which debouches at the end of the probe designed to be situated at the bottom, a gas collection section for collecting the gas which flows out of the gas supply line, which section is situated opposite the debouchment of the gas supply line and is provided with a diaphragm which allows gas through but holds back liquid metal, and a gas removal line which connects to the gas collection section via the diaphragm, which apparatus further contains a gas circuit, one end of which connects to the gas supply line of the probe and the other end of which connects to the gas removal line of the probe, at least one gas detector installed in said circuit and means installed in or on said circuit for causing gas to flow through the circuit, through the gas detector and the probe.

The content of dissolved gases, and in particular hydrogen, in liquid metal has an important effect on the properties of the metal finally obtained. A high concentration of such gases not only results in brittleness of the metal but can also cause serious defects, such as "flakes or gas cavities".

For this reason it is necessary to track the hydrogen content accurately in the case of metal and in particular steel which has to meet high quality requirements, during the manufacturing process and, more particularly, during refining and casting, in order to be able to keep the gas content within defined limits.

Apparatuses of the abovementioned type are especially designed for such hydrogen determination and are intended to replace the current hydrogen determination which consists in collecting a sample of the liquid metal and analyzing it in the laboratory.

With such apparatuses, a small volume of carrier gas may be caused to bubble through the liquid metal. Said gas is collected and passed round a closed circuit several times until an equilibrium has established itself between the gas in the metal and said carrier gas. The gas detector installed in the gas circuit is used to determine the gas content, and more particularly the hydrogen content.

An apparatus of this type is known from British Patent No. 821,821.

In the apparatus according to said patent specification, however, the probe is permanently connected to the circuit and said probe is designed to be used for several consecutive measurements.

Said probe therefore has to be produced from special material which is resistant to long-term residence in a bath of liquid metal, as a result of which said probe is relatively expensive and in practice can only be used for measuring the hydrogen content in baths containing metal having a relatively low melting point.

Even in these cases the service life is limited and the replacment of the probe is fairly time-consuming and expensive.

Said probe has therefore not achieved a breakthrough for measuring the hydrogen content, for example, in liquid metal.

The object of the invention is to remedy said disadvantages and to provide an apparatus for measuring a content in a bath containing liquid metal, said apparatus being relatively cheap to use and making measurement readily possible.

For this object, the device for measuring a gas content of liquid metal contains a lance through which at least a section of the gas circuit extends, which lance contains one part of a quick-connection coupling having a male and a female part which can be coupled to each other, while the probe contains the other parts of the quick-connection coupling on the side facing away from the collection section and at a distance from said collection section, which quick-connection coupling ensures in its coupled state a gastight connection to the gas supply line and the gas removal line of the probe to the sections of the two abovementioned ends of the gas circuit.

The probe is thus constructed as a throwaway probe which is used only for one or at most a limited number of measurements.

The probe therefore only has to be resistant to a relatively short residence in the liquid metal so that it can also be constructed for measurement in metal with a high melting point and can be produced from relatively cheap materials.

The probe is separate from the lance on which the probe can rapidly and readily be fitted before immersion and from which the measuring probe can rapidly and readily be detached. The introduction of the probe is carried out in an easy and safe manner by means of the lance, which can always be reused.

In a particular embodiment of the invention, the probe contains a thermal shield which surrounds the quick-connection coupling and the end of the lance adjacent to the probe.

Said thermal shield has also to withstand the liquid metal only for a limited time and can be produced from cheap materials such as baked sand, paperboard and the like. The gases which are liberated as a result of the possible combustion of said shield have hardly any effect on the measurement since said thermal shield is situated at a relatively large distance from the collecting section.

In an expedient embodiment of the invention, the gas supply line and the gas removal line of the probe are concentric outside the quick-connection coupling part.

Preferably, the outermost line contains a tube which connects the collection section to the quick-connection coupling part of the probe.

In a preferably used embodiment of the invention, the apparatus contains means for opening the gas circuit and connecting the section thereof which communicates with the gas removal line to the open atmosphere.

In this embodiment, at the beginning of the measurement, the carrier gas fed to the gas circuit can be allowed back into the atmosphere and the actual circulation of the carrier gas in a closed circuit through the probe, and thus the actual measurement, may therefore only be started after impurities are detected in the carrier gas for the first time.

In an advantageous embodiment of the invention, the apparatus contains, in the gas circuit, several gas detectors and filters coupled thereto which can retain various gas components from the carrier gas.

With this embodiment, several gas contents can be measured at the same time with the same apparatus.

In a particular embodiment of the invention, the diaphragm is produced from ceramic fibres bound with a binder.

As a result of this, the diaphragm has a low specific gravity and its cooling effect on the liquid metal is extremely low, so that measurement can be carried out in a liquid metal, the temperature of which is close to its solidification temperature.

The invention also relates to the probe from the apparatus according to one of the previous embodiments.

The invention also relates to such a probe, the characteristics of which consist in that the diaphragm has the shape of a bell and the gas collection section is formed by said diaphragm.

From GB A-821,821, an apparatus is known which has a probe, the collection section of which is limited by a bell-shaped wall, but said wall is separate from the diaphragm and not porous.

By giving the diaphragm itself the shape of a bell, the probe is more expedient and its construction is simpler.

The invention also relates to a method for measuring a gas content of a bath of liquid metal, according to which a carrier gas is fed to the gas supply line through a probe which contains a gas supply line and a gas removal line, the lowermost ends of which are situated near each other and which protects into the bath of liquid metal, said carrier gas is collected again after the gas whose content has to be measured has been exchanged with the bath, and it is fed via the gas removal line through a measuring apparatus in which the gas content is measured.

In the apparatus described above, use is made of a throwaway probe which is installed on a lance and is then immersed in the bath.

Said throwaway probe has a limited residence time in the bath so that the measuring cycle, which may begin, for example, with a flushing of the gas lines before the carrier gas is pumped round through the gas detector and the actual measurement therefore begins, has therefore to be carried out fairly rapidly after the immersion.

In said method it may therefore happen that the actual measuring cycle is started too soon or too late.

In methods which use probes which are used for several measurements, it is also advantageous for the service life that the time of immersion of the probe is minimal so that, in these methods too, the measuring cycle should therefore be carried out as rapidly as possible after immersion.

The object of the invention is to remedy this disadvantage and to provide a method for measuring a gas content of liquid metal in which the measuring cycle is always carried out at the required instant.

For this object, a probe is used of which at least one of the gas lines is sealed off by a seal which is opened immediately after immersion of the probe in the bath. Before said closed end is opened, pumping is carried out into the gas line having said end or said line is evacuated, the sudden pressure or flow-rate change on opening the closed end is detected under these circumstances and shortly after said pressure or flow-rate change, the measuring cycle is started and the carrier gas is passed through the probe.

In a particular embodiment of the invention, the measuring apparatus is calibrated when said sudden pressure or flow-rate change occurs.

The carrier gas can be fed to the measuring apparatus immediately after the change is detected via the gas removal line in order to measure the gas content.

In a remarkable embodiment, the measuring cycle is, however, started with a flushing of the lines, carrier gas being fed through the gas lines and being allowed to escape, and only thereafter is carrier gas passed through the probe and through the measuring apparatus for the purpose of the actual measurement.

During the flushing, carrier gas may be fed simultaneously to the gas supply line and the gas removal line, the carrier gas being allowed to escape into the bath.

Carrier gas can also be fed to one of the gas lines of the probe during the flushing and removed via the other gas in tee probe and allowed to escape to the open atmosphere.

During the actual measurement, the carrier gas is preferably pumped in a closed circuit through the probe and the measuring apparatus.

In a particular embodiment of the method according to the invention, a probe is used, the gas removal line of which has a collection section at the bottom which is formed by a section of a tube of the line itself and by a disc-shaped diaphragm which is installed in said section and, on immersion, a carrier gas cushion is created beneath said diaphragm, which cushion is maintained during the measurement so as, in this manner, to prevent contact of the metal with the diaphragm.

In another particular embodiment of the method according to the invention, substances are added to the carrier gas in the colloidal or gaseous state which remove, by reaction, the surface-active substances in the carrier gas bubbles which bubble through the metal and said substances are removed by filtration after passage through the metal.

In this embodiment, it is also possible, for example, to measure the nitrogen content.

In yet another embodiment of the method according to the invention, during the actual measuring cycle, a quantity of the gas component whose content in the metal is to be measured is added to the carrier gas in order to achieve the equilibrium concentration of said gas component in the carrier gas more rapidly.

The invention also relates to a probe which is obviously suitable for the application of the method according to one of the preceding embodiments.

The invention therefore relates to a probe for measuring a gas content of a bath of liquid metal, which probe has a gas supply line, one end of which debouches at the end of the probe designed to be situated at the bottom and a gas removal line for collecting the carrier gas which flows out of the gas supply line whose end is situated in the vicinity of the lowermost end of the gas supply line, and the characteristics of which probe consist in that at least one of the gas lines is sealed by a seal which can be removed during the immersion.

In a particular embodiment of the invention, the lowermost end of the gas supply line is sealed.

In a remarkable embodiment of the invention, the sealed end of the gas line is sealed by a fusible plug which melts during the immersion in the metal bath.

The invention also relates to a method for measuring a gas content, in particular a hydrogen content, of a bath of liquid metal with a low partial pressure of oxygen, according to which method a probe having a gas supply line and a gas removal line, the lowermost ends of which are to be immersed in the bath and are situated near each other, is immersed in the bath, a carrier gas is supplied via a gas line to the gas supply line, said carrier gas is collected again after the gas whose content is to be measured has been exchanged with the bath and fed via the gas removal line of the probe and a gas line connected thereto via a gas detector in which the gas content is measured.

A metal with a low partial pressure of oxygen is a metal with a high $H_2/H_2O$ ratio, such as in the case of, for example, steel.

In known methods for determining the hydrogen content, fairly large correction factors, which cannot always be clearly justified theoretically, are used in the actual measurement based on the hydrogen content which is obtained by exchange in the carrier gas. Although a satisfactory result is obtained with said correction factors at high hydrogen concentrations, this is not the case at low hydrogen concentrations.

The object of the invention is to remedy this disadvantage and to provide a method which makes possible a more accurate measurement of the gas content, in particular of the hydrogen content, without such correction factors having to be used, which method can also be used for very low gas concentrations, in particular hydrogen concentrations, in the metal.

For this object, the carrier gas is dried.

Surprisingly, it has now been found that water or moisture, which is liberated on immersing the probe in the bath from materials from which the probe is constructed, can cause interferences in the measurement. Moisture which is liberated may start to decompose at the high temperatures in the bath so that, in measuring the hydrogen content, not only the hydrogen from the bath is therefore measured, but also the hydrogen produced from the moisture.

For the measurement of other gas contents such as, for example, a nitrogen content, the moisture liberated from the probe also appears to have a disadvantageous effect on the accuracy of the measurement.

By removing the moisture from the gas which is passed through the probe, a very correct measurement is obtained.

In a particular embodiment of the invention, during the measurement, the gas is passed in a closed circuit through the probe and the gas detector, drying of the gas being carried out during this circulation.

The drying can be carried out both in the probe and upstream or downstream of the probe.

The drying can be carried out in the usual manner, either by dry means such as silica gel or, if the drying is carried out outside the probe, by cooling and condensation of the moisture.

The invention consequently also relates to an apparatus for measuring a gas content of a bath of liquid metal with a low partial pressure of oxygen, which apparatus is particularly suitable for carrying out the method according to one of the preceding embodiments.

The invention consequently also relates to an apparatus for measuring a gas content, in particular a hydrogen content, of a bath of liquid metal with a low partial pressure of oxygen, which apparatus contains a probe which is designed to be immersed in the liquid metal and which n its turn has a gas supply line, one end of which debouches at the end of the probe designed to be situated at the bottom, a gas removal line for collecting the gas which flows out of the gas supply line and has exchanged a gas whose content has to be measured from the bath, the end of which removal line is situated in the vicinity of the lowermost end of the gas supply line, which apparatus further contains a gas circuit, one end of which connects to the gas supply line of the probe and the other end of which connects to the gas removal line of the probe, a gas detector installed in said circuit and means installed in or on said circuit for causing carrier gas to flow round the circuit, through the gas detector and the probe, the characteristic of which apparatus consists in that it contains drying means which are installed in or on the entity formed by the gas supply line of the probe, the gas removal line of the probe, the gas circuit and the gas detector.

In a particular embodiment of the invention, the drying means are provided in one of the gas lines in the probe.

Preferably, the apparatus contains a lance and the probe is a throwaway probe which is installed by means of a quick-connection coupling on the lance, of which quick-connection coupling a part is installed on the probe and a part on the lance, and which quick-connection coupling connects the gas supply line and the gas removal line of the probe to both ends of the gas circuit in a gastight manner, the drying means are disposed in one of the gas lines in the probe, the lowermost end of at least one of the gas lines in the probe is sealed in a moisture-tight manner by a seal which is opened when the probe is immersed in the metal oath and the uppermost end of said gas line in the probe is also sealed in a moisture-tight manner by a seal which is opened by coupling the parts of the quick-connection coupling to each other The invention finally relates to a throwaway probe obviously designed to be used in the apparatus according to one of the preceding embodiments.

The invention thus relates to a throwaway probe for measuring a gas content, in particular a hydrogen content, of a bath of liquid metal with a low partial pressure of oxygen, which probe has a gas supply line, one end of which debouches at the end designed to be situated at the bottom, and a gas removal line for collecting a gas which flows out of the gas supply line whose end is situated in the vicinity of the lowermost end of the gas supply line, the characteristic of which throwaway probe consists in that it contains drying means in at least one of the gas lines and said gas line is closed at both ends in a moisture-tight manner by breakable seals.

Other features and advantages of the invention will emerge from the description, which follows below, of an apparatus and a method for measuring a gas content of liquid metal and the probe used therein according to the invention; this description is given solely as an example and does not restrict the invention; the reference numerals relate to the accompanying drawings.

FIG. 4 is partly a front view and partly a section of a filter from the apparatus in FIG. 1.

FIG. 5 is a front view, partly cut away, of a probe similar to that in FIG. 2, but relating to another embodiment of the probe.

In the various figures, the same reference numerals relate to the same elements.

Figure 1:
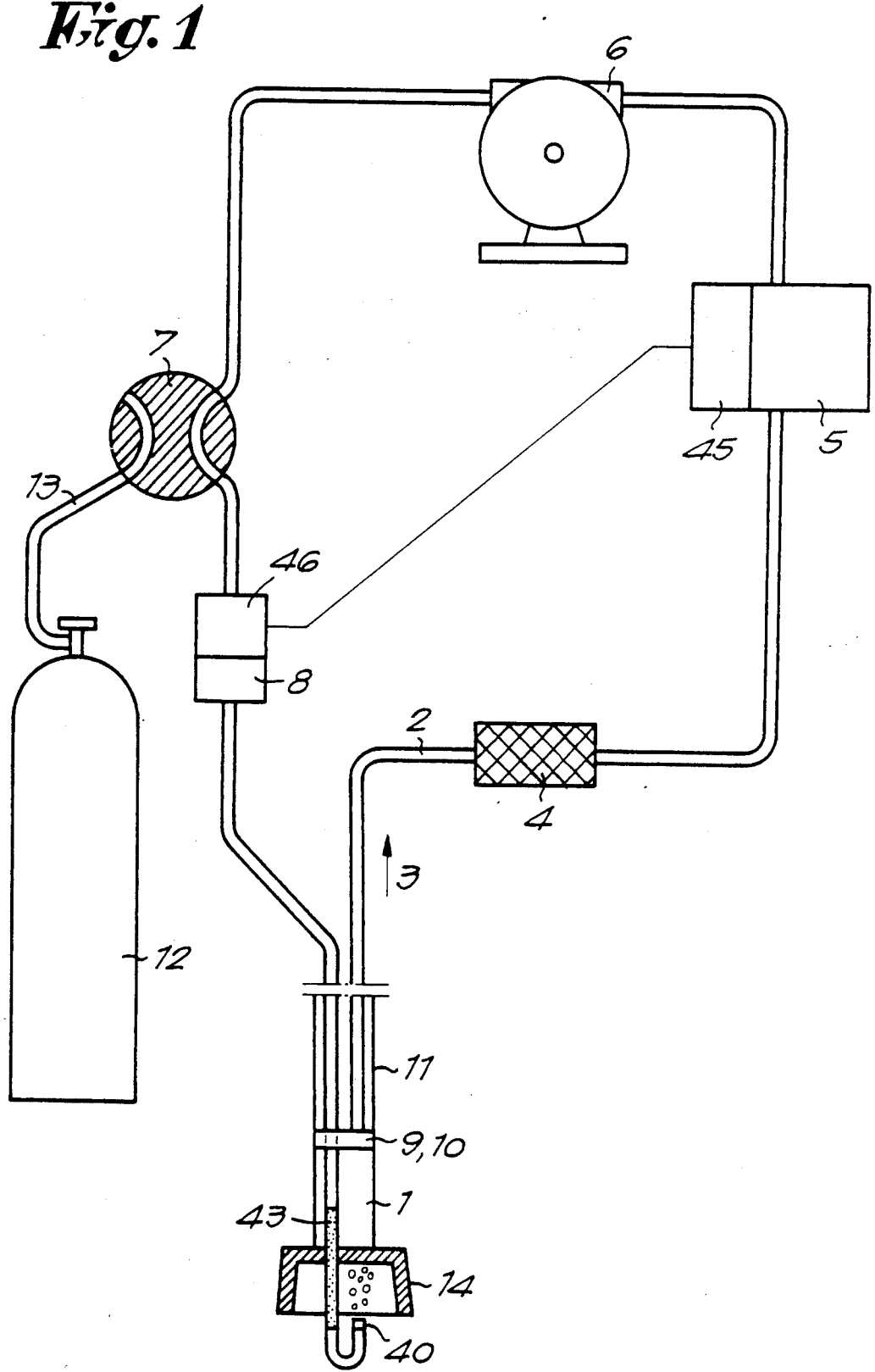
FIG. 1 represents a block diagram of an apparatus for measuring the hydrogen content of liquid steel according to the invention.

The apparatus in FIG. 1 is an apparatus for measuring the hydrogen content in liquid steel.

The apparatus contains essentially a probe 1 and a gas circuit 2, both ends of which connect to the probe and in which a filter 4, a katharometer 5, a pump 6, a four-way stopcock 7, a pressure gauge 46 and a flow meter 8 are installed consecutively in the flow direction of the gas which is indicated in FIG. 1 by the arrow 3.

The probe 1 is a throwaway probe which is connected by means of a quick-connection coupling having a male part 9 and a female part 10 detachably to a lance 11, through which lance ends of the gas circuit 2 extend, and which lance is connected by means of the same quick-connection coupling 9, 10 to said two ends of the circuit 2.

A bottle 12 containing pressurized nitrogen is connected by means of a supply line 13 to the four-way stopcock 7.

Said four-way stopcock 7 closes, in one position, the gas circuit 2, the supply line 13 being connected to the open atmosphere. The bottle 12 is, of course, then closed. In another position, the four-way stop-cock interrupts the gas circuit 2 and it connects, on the one hand, the supply line 13 to the section of the gas circuit 2 which connects to the probe 1 via the pressure gauge 46 and the flow meter 8 and it connects, on the other hand, the section of the gas circuit 2 which comes from the pump 6 to the open atmosphere.

The katharometer 5 is also of a construction known per se and is not described in detail here. Said katharometer determines the hydrogen content of the inert carrier gas by measuring the thermal conductivity of the gas. It is coupled to a microprocessor 45 which is controlled, inter alia, by the pressure gauge 46 and/or the flow meter 8.

Figure 2:
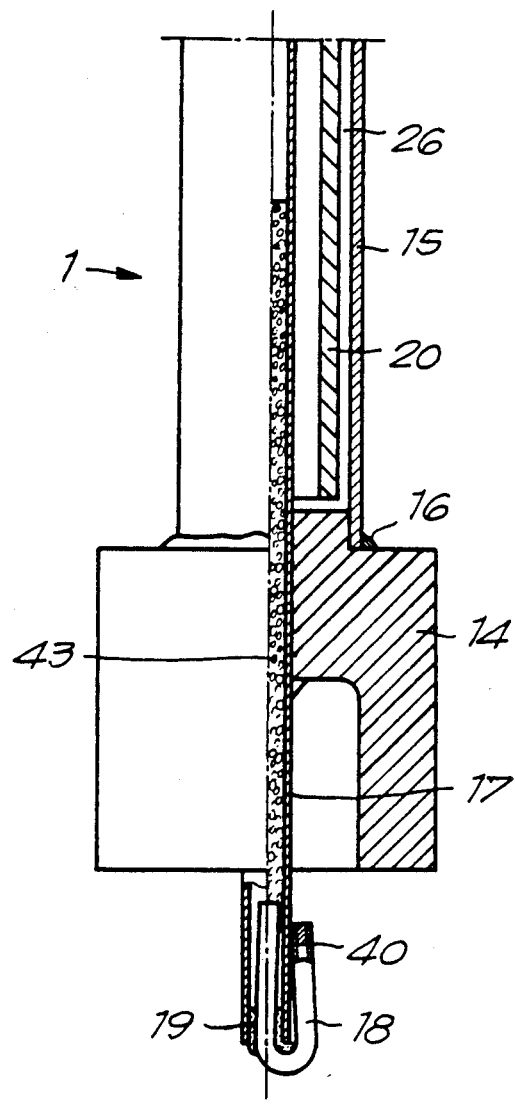
FIG. 2 is partly a section and partly a front view of the lowermost section of the probe from the apparatus in FIG. 1.

The probe 1 contains, as depicted in FIG. 2, at one end a gas collection section which is formed by a diaphragm 14 of porous refractory stone in the shape of a bell and at the other end, the male part 9 of the quick-connection coupling 9, 10 mentioned above.

The opening of the bell-shaped diaphragm 14 is directed away from the part 9 and is held at a distance from said part 9 by a quartz tube 15, to the ends of which the diaphragm 14 and the section 9 are attached by means of cement 16.

Extending axially through the quartz tube 15 is a narrow quartz tube 17 which, on the one hand, projects into the part 9 and, on the other hand, extends through the bell 14 and is attached to said bell-shaped diaphragm 14 with cement.

A limb of a narrower narrow quartz tube 18, bent over 180°, is attached by means of the cement 19 in the open end of the narrow quartz tube 17 extending outside the diaphragm 14. The other end of the limb of said narrow quartz tube 18 is directed with its free end towards the opening of the diaphragm 14. Said end is sealed by a plug 40 of a material which melts at the temperature of the steel bath and which seals the gas supply line 17, 18, 27 before the probe 1 is immersed in the metal bath. The cement 19 seals the tube 17 around the narrow tube 18 in a gastight manner.

In the quartz tube 15, the narrow quartz tube 17 is additionally surrounded by a tube 20 of $Al_2O_3$.

The end of the quartz tube 15 remote from the diaphragm 14 and especially the part 9 of the quick-connection coupling 9, 10 are surrounded by a sheath consisting of three concentric tubes adjacent to each other, namely an innermost tube 21 of paperboard, a middle tube 22 of paperboard and an outermost tube 23 of resin-bonded sand.

The tubes 22 and 23 of said sheath are attached to the quartz tub: 15 by means of cement 24.

The sheath 21, 22, 23 extends at the side facing away from the diaphragm 14 to appreciably beyond the section 9. The inside diameter of the innermost tube 21 corresponds to the outside diameter of the lance 11 whose end projects into said sheath when the lance is connected to the probe 1.

The sheath 21, 22, 23 forms a thermal shield for this lowermost end of the lance 11 and particularly for the quick-connection coupling 9, 10.

Figure 3:
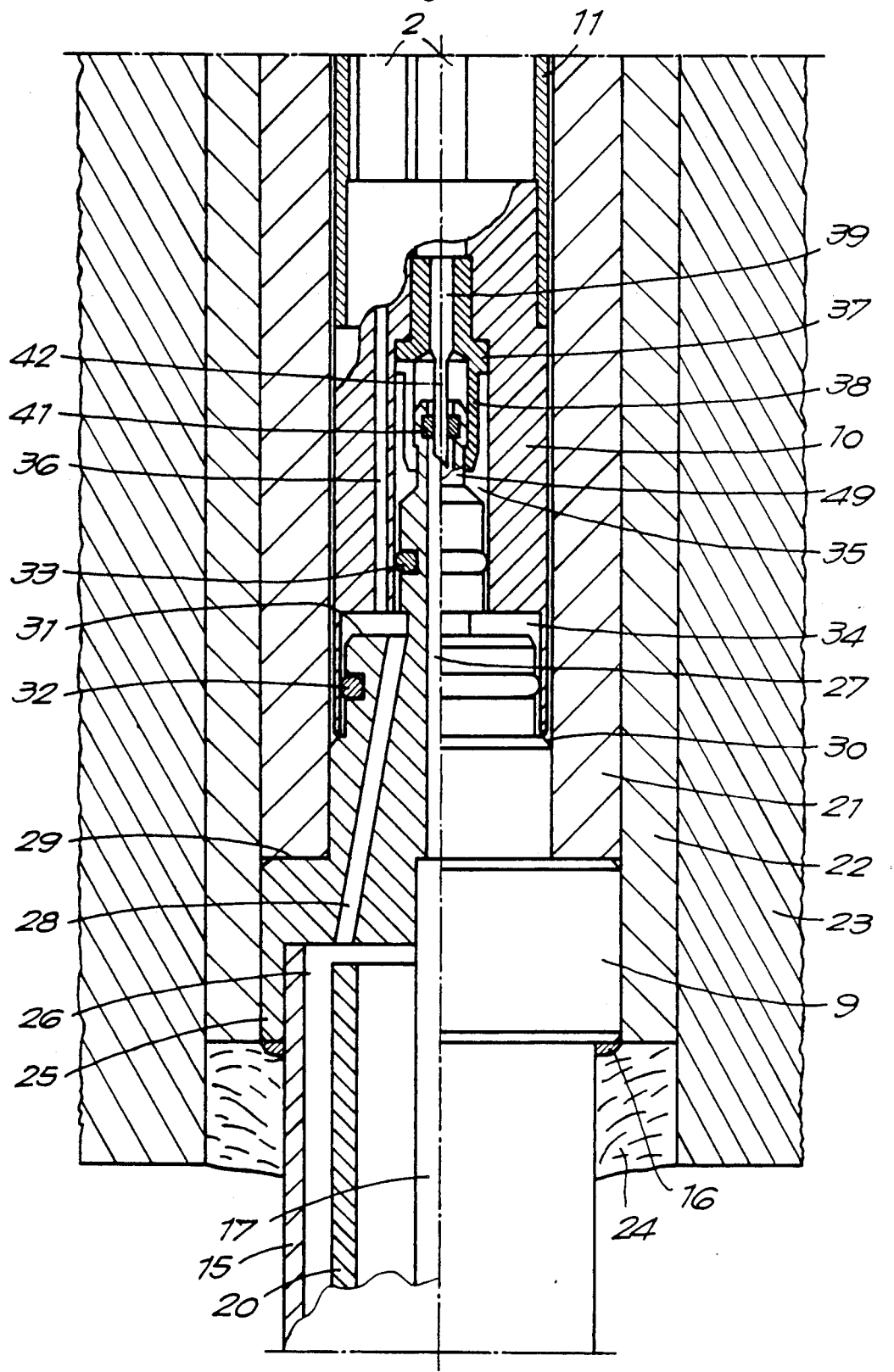
FIG. 3 is partly a section and partly a front view of the uppermost section of the probe from FIG. 1, but drawn on a larger scale than FIG. 2.

As is especially evident from FIG. 3 the male part 9 of the quick-connection coupling 9, 10 consists of a body which, on the immersion side, i.e. the side directed towards the bell-shaped diaphragm 14 is provided with a collar 25 in which the quartz tube 15 is secured and is centrally provided with a hole 26 into which the end of the narrow quartz tube 17 projects.

An axial hole 27, which connects to the hole 26 and forms a gas supply line together with the quartz tubes 17 and 18, extends through said body.

The uppermost end of the axial hole 27 is sealed by a rubber stopper 41 which seals in a moisture-tight manner the hole 27 and therefore the gas supply line 17,18, 27, before the parts 9 and 10 of the quick-connection coupling are coupled, and therefore before the probe 1 is installed on the lance 11.

In addition to the axial hole 27, there extend through the body of the male part 9 four holes 28 which debouch into the space between the quartz tube 15 and the narrow quartz tube 17 and which, together with the last-mentioned space, form a gas removal line which is sealed on the immersion side by the porous diaphragm 14 which forms a diaphragm and allows gas through, but holds back liquid metal. The diameter of the body of the male part 9 of the quick-connection coupling 9, 10 decreases stepwise in the direction facing away from the quartz tube 15 and, specifically, in a manner such that three inwardly indented collars 29, 30 and 31 are formed.

The innermost tube 21 of the sheath 21, 22, 23 is up against the collar 29, situated most outwardly and nearest the quartz tube 15, and is also up against the outside of the cylindrical male part of the section 9 which is situated between the collars 29 and 30.

The section of the body with a smaller diameter which is situated between the collars 30 and 31 is surrounded by an O-ring 32 partly recessed therein.

The abovementioned holes 28 debouch in the collar 31.

The cylindrical section extending outside the collar 31 is also surrounded by an O-ring 33 partly recessed therein.

The collars 30 and 31 and the O-rings 32 and 33 interact with parts of the female part 10 of the quick-connection coupling 9, 10, which female part 10 forms a piece which is installed on the end of the lance 11.

This female part 10 is provided at its end with an axial circular hole 34 into which the cylindrical section, situated between the collars 30 and 31, of the section 9 fits and is provided with a smaller axial hole 35 which, on the one hand, debouches at the base of the hole 34 and, on the other hand, connects to the end of the gas circuit 2 which is situated downstream of the flow meter 8.

Besides the hole 35 there extends, in the part 10, a channel 36 which, on the one hand, debouches at the base of the hole 34 and, on the other hand, connects to the other end of the gas circuit 2 which just like the previous end, is attached in said part 10.

These two ends of the gas circuit therefore extend through the metal lance 11.

In the smallest hole 35 of the part 10 of the quick-connection coupling 9, 10 there is attached a mechanical connecting piece 37 which has four resilient legs 38 provided at their ends with thicker parts which, when the lance 11 is pushed into the sheath 21, 22, 23, are snapped in a resilient manner over the thickened head on the end of the male part 9 projecting outside the collar 31.

When the lance 11 is pushed to the maximum extent into the sheath 21, 22, 23, as shown in FIG. 3, the thickened parts on the ends of the legs 38 hook behind an outwardly directed collar formed at the point of the groove 49 in the end of the part 9 of the quick-connection coupling 9, 10 projecting out of the collar 31.

The connecting piece 37 is provided with a channel 39, so that the hole 35 remains in communication with the end of the circuit 2.

In the fully pushed-in position of the lance 11, an end of the section 10 is up against the collar 30 of the male part 9 and the inside wall of the hole 34 is up against the O-ring 32 in a gastight manner.

The inside wall of the hole 35 is up against the O-ring 33 in a gastight manner.

In this manner, the probe 1 is connected mechanically to the lance 11 by the connecting piece 37, but nevertheless detachably since, by exerting sufficient force the legs 38 are able to spring apart so as to slide over the thickened end of the male part 9.

The gas removal line 15, 28 of the probe 1 formed by the tube 15 around the tube 17, and the hole 28 connects in a gastight manner via the channel 36 to one end of the gas circuit 2, while the gas supply line 17, 18, 27 formed by the tubes 17 and 18 and the hole 27 connect in a gastight manner to the other end of the gas circuit 2 via the central hole 35. In the coupled state of the quick-connection coupling 9, 10, a partion of the hole 34 extending symmetrically around the male part 9 forms the connection between the hole 28 in the part 9 and the channel 36 in the female part 10, while the axial hole 27 in the male part 9 connects via the hole 35 to the channel 39 in the female part 10 and, consequently, to the end of the circuit through which gas is fed to the probe 1. The female part 10 can therefore be coupled in any position whatever of the male part 9 and the lance 11 does not therefore have to be pushed into the sheath 21, 22, 23 in a well-defined position.

In a variant of the embodiment described above, the porous diaphragm 14 is produced from ceramic fibres bound to each other by a binder, instead of from porous stone. This makes it possible to carry out measurements in liquid metal whose temperature is close to the solidification temperature.

Connected to the connecting piece 37 is a hollow needle 42 which extends axially between the legs 38 and whose hollow part connects to an axial channel 39 transversely through the connecting piece 37.

To install the probe 1 on the lance 11, the needle 42 is forced through the rubber stopper 41 into the hole 27 of the male part 9, so that if the legs 38 of the female part 10 are snapped over the thickened head of the male part 9, the needle 42 protects through the stopper 41 and connects the hole 35 of the gas supply line 17, 18, 27 with one end of the circuit 2 situated in the centre of the lance and downstream of the flow meter 8.

As is especially evident from FIG. 2, the quartz tube 17 of the gas supply line 17, 18, 27 is partly filled with silica gel 43.

Because said gas supply line is sealed in a moisture-tight manner at both ends, respectively by the fusible plug 40 and the rubber stopper 41, as a result of mounting the probe 1 on the lance 11, the drying means formed by the silica gel 43 does not absorb any moisture from the air.

The entity formed by the quartz tube 15 with possibly the bell-shaped diaphragm 14, the projecting end of the narrow quartz tube 17 and the narrow quartz tube 18 may also be surrounded by a cap of metal which, for the sake of simplicity, is not depicted in the figures and is attached to the sheath 21, 22, 23 and which is surrounded by a cap of paperboard, likewise not shown in the figures.

The cap of paperboard prevents the slag sticking to the metal cap if the probe 1 is introduced through a slag which is situated on the liquid metal, which metal cap prevents the probe 1 being damaged when the latter is introduced through the slag.

During the introduction, the paperboard cap is burnt, while immediately after the introduction, the metal cap melts, whereafter the measurement can be carried out in the manner described below.

As is evident from FIG. 4, the filter 4 contains a tube 47 which is closed at one end and to the other, open end of which there connects a male part 44 of the quick-connection coupling which is identical to the abovementioned male part 9 of the quick-connection coupling 9, 10. Corresponding parts of the male part 44 have been given the same reference numeral as in the male part 9.

There extends axially in the tube 47 a narrow tube 48 which is open at both ends and one end of which terminates at a distance from the closed end of the tube 47 and the other end of which is secured in the male part 44 and debouches into the axial hole 27 of the male part 44.

The space between the narrow tube 48 and the tube 47, which space connects to the holes 28 in the male part 44, is filled with filter material 50.

The female part of the quick-connection coupling which interacts with the male part 44 is installed in the gas circuit 2, which female part is identical to the abovementioned female part 10 of the quick-connection coupling 9, 10.

For the sake of simplicity, said second section is not shown in the figures.

The hole 35 and the channel 39 of said second section connect to the section of the gas circuit 2 which connects directly to the probe 1, while the channel 36 and the hole 34 of said second sect on communicate with the section of the gas circuit 2 which connects to the katharometer 5.

In this manner, said quick-connection coupling forms, in the same manner as the quick-connection coupling 9, 10, not only a rapid connection of the detachable filter to the gas circuit 2, but also the junction of two axial lines, namely the tube 47 and the narrow tube 48, with two parallel lines, namely the sections of the gas circuit 2 on either side of the filter 4.

To carry out a measurement, the probe 1 is installed by mean of the quick-connect on coupling 9, 10 on a lance 11, which lance is therefore pushed into the sheath 21, 22, 23 of the probe 1, as a result of which the seal, formed by the rubber stopper 41, of the uppermost end of the gas supply line 17, 18, 27 is opened by the needle 42, as described above.

The four-way stopcock 7 is set in the position in which the supply line 13 connects to the gas circuit 2, so that nitrogen flows from the bottle 12 to the probe 1.

Because the lowermost end of the gas supply line 17, 18, 27 is still sealed by the fusible plug 40, nitrogen will no longer flow once said line has been filled and a relatively high pressure, which corresponds to the pressure of the gas bottle 12, will prevail in said line.

As soon as the probe 1 is immersed in the bath of liquid steel, the plug 40 melts and nitrogen bubbles through the liquid metal, which nitrogen is collected in the bell-shaped diaphragm 14 and is drawn off via the gas removal line 15, 28 and the circuit 2 via the filter 4 and the katharometer 5 by the pump 6, which has been started in the meantime. The melting of the plug 40 therefore defines the start of the measurement cycle which starts in turn with a flushing.

For a few seconds, the gas drawn off escapes at the position of the four-way stopcock 7 into the open atmosphere, as a result of which any impurities which are produced when the probe 1 is immersed in the metal bath, for example by combustion of constituents of the probe, are removed.

Either after flushing for ten seconds or when the katharometer no longer measures any impurities, the microprocessor 45 alters the position of the four-way stopcock to the position shown in FIG. 1, in which the nitrogen consequently flows in a closed circuit around the circuit 2 and the probe 1 and the actual measurement begins.

Even during the flushing, but also while nitrogen is circulating, any moisture which is still released, for example, from the probe 1, is absorbed by the silica gel 43 in the narrow tube 17, so that no moisture is fed into the metal bath with the nitrogen and neither is any additional hydrogen consequently produced by liberated moisture.

After the dried nitrogen which has exchanged hydrogen with the metal bath has been pumped round for a short time, an equilibrium is established in relation to the hydrogen and the katharometer 5 indicates the correct hydrogen content.

As a result of the absence of additional hydrogen which has been formed by moisture, no correction factor has to be applied and it is possible for even very low hydrogen contents to be measured.

In a variant of the method described above, a probe 1 is used, of which not only the gas supply line 17, 18, 27, but also the gas removal line 15, 28 is sealed in an airtight manner at the lowermost end by a plug which melts on immersion in the bath.

Because the bell-shaped diaphragm 14 is porous, said seal should then be provided at the lowermost end of the quartz tube 15.

The same device as in FIG. 1 is used in that case, but the four-way stopcock 7 is replaced by a more complicated distribution device, so that, before the immersion, pressurized nitrogen from the gas bottle 12 is fed via both sections of the circuit, both to the gas supply line 17, 18, 27 and to the gas removal line and, more particularly, the section 15, 28 thereof.

As soon as the probe 1 is immersed, not only the abovementioned plug 40 melts, but also the plug in the quartz tube 15.

The sudden flow-rate or pressure change which is produced when the plugs melt away is measured and immediately after said changes, the position of the distribution valve is changed and the operation of the katharometer 5 is started via the microprocessor 45 and the measuring cycle is therefore started as in the embodiment described above.

In this variant, the microprocessor 45 can be controlled by a pressure gauge 46 which is installed in the section of the circuit 2 which connects to the gas removal line 15, 28. Said pressure gauge may in that case even be incorporated in the katharometer.

In yet another embodiment of the method the procedure is as in the variant described above, but the position of the distribution valve is not changed immediately when the sudden flow-rate or pressure change occurs when the plugs in the gas lines 15, 28 and 17, 18, 27 melt away.

The flushing at the beginning of the measuring cycle is therefore carried out both by carrier gas which is blown through the flow-rate meter 8, a section of the circuit 2 and the gas supply line 17, 18, 27 into the metal bath and by carrier gas which is also blown into the metal bath via the rest of the circuit 2, through the pump 6, which may possibly facilitate the flow of the carrier gas by rotating in the required direction, and the gas removal line 15, 28.

Ten seconds after this blowing, the position of the distribution valve is in fact changed and the carrier gas is then fed in a closed circuit through the circuit 2 and the probe 1 and the actual measurement by the katharometer 5 therefore takes place.

In all the embodiments described above, the measurement takes place at the correct instant, so that the measurement is always terminated before the probe 1 is destroyed by the heat of the metal bath.

The drying means may be provided in the probe 1 in the gas removal line 15, 28 instead of in the gas supply line 17, 18, 27 or they may be provided in both lines or even outside the probe anywhere in the gas circuit 2. For example, the filter 4 from the circuit 2 may be filled with silica gel or another drying agent, instead of with filter material.

The drying means can also be provided in the katharometer 5.

It is important that no moisture enters the bath of liquid metal during the actual measurement.

If drying means are provided in the circuit, they may also be formed by cooling means which remove the moisture from the gas in the circuit by condensation.

The variant of the probe 1 shown in FIG. 5 differs from the embodiment shown in FIGS. 2 and 3, in that the collection section is not formed by a porous bell-shaped diaphragm 14 but in fact by the immersion end of the quartz tube 15 itself and by the disc-shaped diaphragm 51 of porous ceramic material which closes off said tube around the actual quartz tube 17 at a distance from the open end of the quartz tube 15 and allows gas, but no liquid metal, through, and in that the tube 20 of $Al_2O_3$ is replaced by a mass of small balls 52 which fill the space around the axial quartz tube 17 and between the disc-shaped diaphragm 51 and the male part 9 of the quick-connection coupling 9, 10. Said small balls 52 do not prevent the passage of gas, so that the space between the quartz tube 15 and the central quartz tube 17 still forms part of the gas removal line of the probe 1 debouching at the porous disc-shaped diaphragm 51. For the sake of simplicity, the sheath 21, 22, 23 of the probe 1 s not shown in FIG. 5.

In said embodiment, a few granules 53 of a chemical element which forms stable oxides, such as chromium, zinc, titanium, aluminium, zirconium, calcium magnesium, or a lanthanide element are situated just above the disc-shaped diaphragm 51 in the tube 15. In particular, zinc, magnesium and calcium are appropriate since they are gaseous at the temperatures used and are particularly reactive. If the material of the diaphragm contains unstable oxides, said elements prevent hydrogen from the metal bath being converted into water, which would affect the measurement.

Instead of granules of said elements, a thin layer of the element may be provided in a section of the tube 15 or the tube 17.

The method for measuring with said probe is analogous to the method described above.

When the probe 1 is immersed in the liquid metal, said metal solidifies for a short time against the diaphragm 51, as a result of which the gas removal temporarily becomes impossible. The measuring cycle can only start after a temperature equilibrium has established itself and said solidified metal is liquid again.

In order to prevent this and, consequently, to make more rapid measurement possible, the contact of the liquid metal with the porous disc-shaped diaphragm 51 can be prevented by forming a gas cushion under said diaphragm. The gas cushion is formed by the carrier gas itself. The diaphragm 51 has a relatively high flow resistance, as a result of which a pressure difference exists across said diaphragm. At the highest-pressure side which is the bath side, a gas cushion at pressure $P_2$ can be formed, while at the other side, the gas diffusing through the diaphragm is removed at a lower pressure $P_1$.

The flow resistance differs, however, from diaphragm to diaphragm and is not constant during measurement cycle. The pressure $P_2$ of the gas cushion has therefore to be actively regulated, and this can be done by the flow-rate regulating valve incorporated in the flow-rate meter 8, the level 54 of the liquid metal in the probe 1 being detected by a sensor 55 which is formed by two electrical contacts which are secured at a distance below the disc-shaped diaphragm 51 in the tube 15.

In this embodiment, use is made of a multi-way stopcock 7 which, in the initial setting, in which carrier gas is fed into the circuit from the bottle 12, feeds it not only via the flow meter 8 and the pressure meter 46 to the gas supply line 17, 18, 27 which is still closed by the plug 40, but also through the not yet operational pump 6 and katharometer 5 to the gas removal line 15, 28 of the probe 7.

As a result of this, during the immersion of the probe 1, a very high pressure is produced above the diaphragm 51 and the metal cannot come into contact with the diaphragm 51.

As soon as the plug 40 melts, a gas flow with a high flow rate is produced through the probe 1 and the metal bath and consequently, also through the, diaphragm 51. Carrier gas is now drawn off by means of the pump 6 along the gas removal line 15, 28, as a result of which the pressure above the diaphragm 51 falls. By adjusting the correct flow rate of the carrier gas, the gas cushion below the diaphragm 51 can be maintained, even after flushing and during the actual measurement cycle, during which the carrier gas is caused to flow in a closed circuit round the circuit 2, the probe 1 and the metal bath.

With this embodiment it is also possible to make measurements in liquid metals with a high partial pressure of oxygen, such as copper. The gas cushion prevents oxides forming in the diaphragm 51, which gradually cause said diaphragm to become blocked up.

Figure 6:
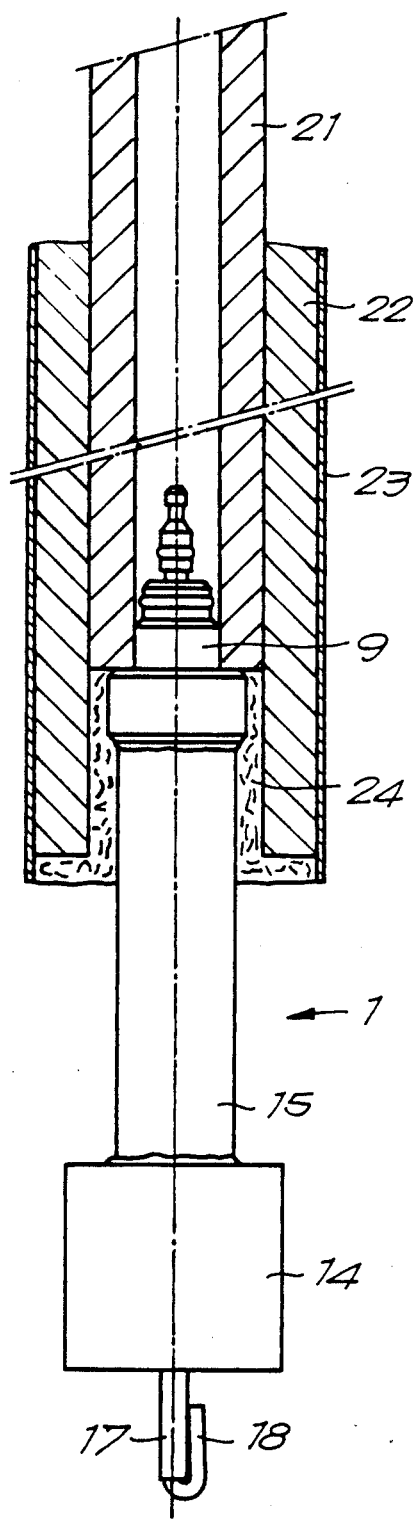
FIG. 6 is a front view, partly cut away, of a probe similar to those in FIGS. 2 and 3 or 4, but relating to yet another embodiment of the probe.

The embodiment of the probe 1 shown in FIG. 6 differs from the embodiment in FIGS. 2 and 3 simply and solely as a result of a different construction of the sheath 21, 22, 23 which forms the thermal shield of the quick-connection coupling 9, 10.

Although the innermost tube 21 is also produced from paperboard, the outermost tube 23 is a very thin paperboard tube, while the middle tube 22 is formed by means of resin-bonded sand.

The production of this sheath is fairly easy. It is sufficient to introduce the sand together with the resin between the tubes 21 and 23 and to bake this entity in a furnace. The outermost tube 23 of paperboard protects the resin-bonded sand.

In yet another embodiment, said outermost tube 23 is produced from tinplate or even from plastic instead of from paperboard The outermost tube 23 may optionally be coated with a non-splash layer.

By using filters based on zeolites and several katharometers, the apparatuses described above may be used not only to measure, for example, the hydrogen content, but also to measure the content of other gas components simultaneously. For this purpose, in the apparatus as shown in FIG. 1, the katharometer 5 is replaced by a battery of katharometers connected in series, a gas component to be determined being filtered out of the gas after each katharometer except after the last one. The determination of the hydrogen, carbon monoxide and nitrogen content of a metal bath is carried out as follows. In the first katharometer, the total partial pressure of $H_2$, CO and $N_2$ and carrier gas is measured. The carrier gas then flows through the hydrogen filter based on zeolites in which hydrogen is filtered out. The filtered gas then flows through a second katharometer, which measures the total partial pressure of CO, $N_2$ and carrier gas. After a CO filter which retains the CO, a third katharometer measures the partial pressure of $N_2$ and carrier gas. After filtering out $N_2$ in a third filter based on zeolites, a fourth katharometer measures the partial pressure of the carrier gas. By subtracting the measurement results from each other, the partial pressure of each of the gas components can thus be calculated separately. The difference between the measurement signals of the second and third katharometers gives, for example, the CO partial pressure.

During the measurement of some gases, for example nitrogen, the transfer of the gas dissolved in the metal to the bubble of carrier gas which is bubbling through the metal bath may be impeded by surface-active substances (for example oxygen and sulphur) which are located on the inside wall of the gas bubble.

To prevent this, said surface-active substances are removed by a reaction as a result of adding substances to the carrier gas in the colloidal or gaseous state, such as, for example, magnesium or calcium. Said substances are retained after reaction and upstream of the katharometer 5 by the filter 4 or an additional filter.

To shorten the time in which a good estimate of the equilibrium concentration of the gas component in the metal bath to be measured can be obtained and, in the case of very low concentrations of the gas component to be measured in the metal bath, to prevent a relatively substantial fraction of said component being entrained with the carrier gas and thus disappearing from the bath as a result of the measurement itself, a quantity of the gas component to be measured may be added to the carrier gas during the actual measurement. This may be carried out either as a function of the measured change in the concentration of the gas to be measured in the carrier gas in the course of consecutive circulations, or in accordance with a pre-programmed pattern.

According to the first method, after the first circulation of the carrier gas in which the concentration of the gas component to be measured was known, the change of concentration of said gas component to be measured is measured by means of the probe 1 and the metal bath. The equilibrium concentration is estimated by means of a known pre-programmed saturation curve. Gas is added to the carrier gas until the concentration of said component almost reaches the estimated equilibrium concentration. After this mixture of carrier gas and the gas component to be measured have been circulated, the change in concentration is measured again and the equilibrium concentration is again estimated in a similar manner. This procedure is repeated, if necessary, until the desired accuracy is achieved.

According to the second method, before a circulation of the carrier gas, the concentration of the gas component to be measured in the carrier gas is measured in a known manner continuously or stepwise. The profile of the concentration of gas component as a function of time is therefore known.

After a first circulation of the carrier gas through the probe 1 and the metal bath, the katharometer detects an altered profile of the concentration of gas component as a function of time.

Allowing for the time shift between the two profiles, the point of intersection of the abovementioned profiles before the circulation of the carrier gas through the metal bath and the profile after circulation gives the required equilibrium concentration.

The measurement n the manner described above and with the apparatuses described above is very simple and rapid. For each measurement, it is only necessary for the probe to be replaced. The rest of the apparatus can always be used again.

As a result of the quick-connection coupling, a replacement of the probe can be carried out very easily and rapidly. The filter can also be replaced rapidly as a result of the quick-connection coupling.

The invention is by no means restricted to the embodiments described above and, within the scope of the Patent Application, many changes can be made to the embodiments described in relation to the shape, the construction, the arrangement, and the number of components which are used to implement the invention.

In particular, the various parts of the probe do not necessarily have to be produced from the materials described above. Said materials depend, inter alia, on the metal bath in which measurement is carried out.

Thus, the diaphragm formed by the bell or the disc does not necessarily have to be of porous stone. Said diaphragm may, for example, also be produced from ceramic fibres.

The outermost tube of the probe does not necessarily have to be produced from quartz either. Said tube may also be produced from metal which is coated with a ceramic material. To carry out measurements in liquid copper, the tube may be manufactured from uncoated steel.

In the embodiment in which the lowermost section of the outermost tube itself forms the collection section along with the diaphragm, the complete tube may be produced from porous material, the uppermost end of which is provided with a gastight and heat-resistant coating and the lowermost section of which forms a porous collection section together with the diaphragm.

The thermal shield does not necessarily have to consist of three concentric tubes. Said thermal shield may, for example, consist of a single sheath of resinbonded sand or of paperboard.

The measuring instrument in the gas circuit does not necessarily have to be a katharometer. Other detection instruments which are able to measure a gas in the carrier gas may be used. For measuring CO, $CO_2$, $SO_2$ and $H_2S$, it is possible, for example, to use a measuring instrument based on infrared radiation.

The mechanical coupling of the parts of the quick-connection coupling does not necessarily have to be made by resilient legs on the part which belongs to the lance. The part which belongs to the probe may be provided with resilient legs or be otherwise deformable in a resilient manner. The coupling has only to make a reliable mechanical connection possible which can be undone by exerting sufficient tensile force.

We claim:

1. An apparatus for measuring a gas content of liquid metal, said apparatus comprising a probe for being immersed in the liquid metal, said probe including a gas supply line which debouches at an end of the probe, a gas collection section for collecting a gas flowing out of the gas supply line, said gas collection section being positioned for receiving the gas flowing from the debouchment of the gas supply line and being provided with a diaphragm permeable for gas but impermeable for liquid metal, a gas removal line in fluid communication with the gas collection section, a gas circuit having a first end in fluid communication with the gas supply line of the probe and a second end in fluid communication with the gas removal line of the probe, at least one gas detector in fluid communication with said circuit, gas moving means in fluid communication with said circuit for moving gas through the circuit, the gas detector and the probe, a lance through which at least a section of the gas circuit extends, and a quick-connection coupling having two parts which can be coupled to each other, said lance containing one part of said quick-connection coupling, said probe containing the other part of the quick-connection coupling, said quick-connection coupling providing in the coupled state, a gastight connection of the gas supply line and the gas removal line to the first and second ends of the gas circuit.

2. The apparatus of claim 1, further including a thermal shield surrounding the quick-connection coupling and an end of the lance adjacent to the probe.

3. The apparatus of claim 2, wherein the thermal shield includes at least one tube of resin-bonded sand and at least one concentric tube of paperboard surrounding the quick-connection coupling.

4. The apparatus of claim 2, wherein said thermal shield includes an innermost tube of paperboard positioned within a thin outermost tube of paperboard such that a spaced is formed therebetween, said space being filled with resin-bonded sand to thereby form a middle tube.

5. The apparatus of claim 1, wherein said quick-connection coupling includes coupling means for coupling the two parts thereof detachably to each other, said coupling means including resilient legs on one part and a collar on the other part of the quick-connection coupling.

6. The apparatus of claim 1, wherein the gas supply line and the gas removal line of the probe are concentrically positioned outwardly of the quick-connection coupling.

7. The apparatus according to claim 6, wherein said quick-connection coupling couples the supply and gas removal lines to the gas circuit regardless of a relative angular position of one part of said quick-connection coupling with respect to the other part of said quick-connection coupling.

8. The apparatus of claim 6, wherein the gas removal line includes a tube, said tube connecting the collection section to the quick-connection coupling part of the probe.

9. The apparatus of claim 6, wherein the first and second ends of the gas circuit extend generally parallel to each other and the quick-connection coupling contains a junction of said parallel ends to the supply and gas removal lines.

10. The apparatus according to claim 7, wherein the part of the quick-connection coupling on the probe includes an axial conduit and at least one adjacently situated conduit, said part of the quick-connection coupling on said lance includes an axial conduit and an adjacently situated channel and in the coupled condition of said parts both said axial conduits connect to each other and an annular space which is completely separated from said axial conduits couples the adjacently situated conduit to the adjacently situated channel.

11. The apparatus of claim 1, wherein one part of the quick-connection coupling includes two sealing rings for providing a gastight connection of both quick-connecting coupling parts in the coupled condition.

12. The apparatus of claim 1, further including opening means for opening the gas circuit and connecting a section thereof which communicates with the gas removal line to the open atmosphere.

13. The apparatus of claim 12, further including a source of inert gas and a second supply line between said source and the gas circuit, said opening means being comprised of a stopcock having one position, wherein the gas circuit is closed and another position wherein the section of the gas circuit in fluid communication with the gas removal line is open to the atmosphere and connects another section of the gas circuit in fluid communication with the gas supply line of the probe to said second supply line between said source and gas circuit.

14. The apparatus according to claim 1, wherein the gas circuit further includes at least one filter coupled to the gas detector for filtering various gas components flowing through the gas circuit.

15. The apparatus of claim 14, wherein the gas circuit includes a first gas detector, a filter for a first gas component, a second gas detector, and a second filter for a second gas component.

16. A probe comprising a gas supply line which debouches at one end of the probe, a gas collection section for collecting gas flowing out of the gas supply line, said gas collection section being positioned for receiving the gas flowing from the debouchment of the gas supply line and including a diaphragm permeable for gas but impermeable for liquid metal, a gas removal line in fluid communication with the gas collection section, and a part of a two-part quick-connection coupling mounted on another end of said probe for detachably receiving another part of said two-part quick-connection coupling mounted on an end of a lance.

17. The probe of claim 16, in which the diaphragm is constructed of ceramic fibers bound with a binder.

18. The probe of claim 16, in which the diaphragm is constructed of porous stone.

19. The probe of claim 17, in which the diaphragm is generally bell-shaped to thereby form the gas collection section.

20. The probe of claim 17, in which the gas collection section is formed by a section of a tube having the gas removal line and a disc-shaped diaphragm therein, said probe including a level detector positioned beneath the diaphragm in said section.

21. A method for measuring a gas content of a bath of liquid metal, said method comprising the steps of:
providing a probe having a gas supply line and a gas removal line each having a lowermost end positioned proximate the other for being immersed in the bath;
sealing the lowermost end of at least one of the gas lines with a seal which opens immediately after immersion in the bath;
pumping carrier gas into the gas line having said sealed end;
immersing said probe in said bath of liquid metal such that said seal opens;
detecting a sudden pressure or flow-rate change in one of the gas lines;
passing carrier gas through the probe to thereby start a measurement cycle;
collecting the carrier gas in the course of the measurement cycle after exchanging with the bath the gas whose content is to be measured;
feeding the carrier gas through the gas removal line into a measuring apparatus; and
measuring the gas content with said measuring apparatus.

22. The method of claim 21, further comprising the step of calibrating said measuring apparatus upon detecting said sudden pressure or flow-rate change.

23. The method of claim 21, wherein the step of passing carrier gas through the probe to start the measurement cycle comprises the steps of flushing the lines, feeding carrier gas through said lines, and allowing said carrier gas to escape into the open atmosphere.

24. The method of claim 23, wherein the step of flushing the lines further comprises simultaneously feeding said carrier gas into the gas supply line and the gas removal line for allowing the carrier gas to escape into the bath.

25. The method of claim 23, wherein the step of flushing the lines further comprises the steps of feeding carrier gas into one of the gas lines of the probe; removing the carrier gas through the other gas line in the probe and allowing the carrier gas to escape into the open atmosphere.

26. The method of claim 23, wherein the step of flushing is carried out for 1 to 10 seconds.

27. The method of claim 21, wherein the step of passing carrier gas through the probe to start a measurement cycle comprises the step of pumping the carrier gas in a closed circuit through the probe and the measuring apparatus.

28. The method of claim 21, wherein the step of sealing the lowermost end of the gas line comprises the step of positioning a fusible stopper within the gas line, the stopper being of a type which melts upon immersion in the bath.

29. The method of claim 28, wherein the step of sealing the lowermost end comprises the step of sealing the gas supply line with the fusible stopper.

30. The method of claim 23, further comprising the steps of providing said lowermost end of said gas removal line with a gas collection section, said gas collection section being formed of said gas removal line and a disc-shaped diaphragm; and wherein the step of immersing said probe comprises the step of creating a carrier gas cushion beneath said diaphragm and maintaining said cushion during said measuring step to prevent contact of the metal with the diaphragm.

31. The method of claim 23, further comprising the steps of filtering the carrier gas substances in the colloidal or gaseous state for removal of the surface-active substances in the carrier gas bubbles after passage through the metal.

32. The method of claim 23, further comprising the step of adding a quantity of the gas component whose content in the metal is to be measured to the carrier gas for achieving a rapid equilibrium concentration of said gas component in the carrier gas.

33. The method of claim 32, wherein the step of measuring further comprises the steps of:
feeding carrier gas into a closed circuit in fluid communication with the probe and a gas detector;
measuring the change of concentration of the gas component in the carrier gas after at least a circulation of the carrier gas through said circuit;
estimating an equilibrium concentration on the basis of a known, pre-programmed saturation curve;
adding the gas component to the carrier gas until the concentration of said component almost reaches the estimated equilibrium concentration;
measuring the concentration change of said component after a subsequent circulation of the carrier gas;
estimating an equilibrium concentration in an analogous manner; and
repeating one or more of the above steps until the estimated concentration is sufficiently accurate.

34. The method of claim 32, wherein the step of measuring further comprises the steps of:
feeding carrier gas into a closed circuit in fluid communication with the probe and a gas detector;
varying the concentration of a gas component to be measured in the carrier gas before a complete circulation of the carrier gas around the circuit;
obtaining a concentration profile of the gas component to be measured as a function of time after said circulation of the carrier gas;
measuring an altered profile of concentration as a function of time; and
comparing said altered profile with the preceding profile and, allowing for the delay resulting from the circulation time.

35. A probe for measuring a gas content of a bath of liquid metal, said probe comprising a gas supply line having a lowermost end which debouches at an end of the probe and a gas removal line having a lowermost end for collecting carrier gas flowing out of the gas supply line, said lowermost end of said gas removal line being positioned proximate the lowermost end of the gas supply line, at least one of the gas lines being sealed by a seal removable during immersion of the probe into the liquid metal.

36. The probe of claim 35, wherein the lowermost end of the gas supply line is sealed.

37. The probe of claim 35, wherein said seal is a fusible plug which melts during immersion into the liquid metal.

38. The probe of claim 35, wherein said probe is disposable and includes means for detachably coupling the probe to a lance.

39. A method for measuring a gas content, in particular a hydrogen content, of a bath of liquid metal with a low partial pressure of oxygen, said method comprising the steps of:
providing a probe having a gas supply line and a gas removal line, each having a lowermost end positioned proximate the other;
immersing said lowermost ends in the liquid metal;
supplying a carrier gas to the gas supply line;
collecting said carrier gas after hydrogen gas has been exchanged with the bath;
feeding said hydrogen gas into the gas removal line of the probe to a gas detector;
measuring the hydrogen gas content; and
drying the hydrogen gas before the end of the measuring.

40. The method according to claim 39, wherein the step of measuring further comprises the step of circulating the hydrogen gas through a closed circuit, the probe, and the gas detector, said drying step of the gas being carried out during such circulation.

41. An apparatus for measuring a gas content, in particular a hydrogen content, of a bath of liquid metal with a low partial pressure of oxygen, said apparatus comprising a probe for immersion into the liquid metal, said probe including a gas supply line having an uppermost end and a lowermost end which debouches at an end of the probe and a gas removal line having an uppermost end and a lowermost end for collecting gas flowing out of the gas supply line and for collecting hydrogen gas from the bath, the lowermost end of the said gas removal line being positioned proximate the lowermost end of the gas supply line, a gas circuit having one end in fluid communication with the gas supply line and another end in fluid communication with the gas supply line, said circuit including a gas detector and gas movement means for moving carrier gas through the circuit, the gas detector and the probe, and drying means for drying said carrier gas positioned within the gas supply line of the probe, the gas removal line of the probe, the gas circuit and the gas detector.

42. The apparatus of claim 41, wherein the drying means is positioned within one of the gas lines.

43. The apparatus of claim 41, wherein the probe is disposable and further including a lance, a quick-connection coupling for connecting said probe to said lance, part of said quick-connection coupling being installed on the probe and another part of the coupling being installed on the lance, said quick-connection coupling connecting the gas supply line and the gas removal line of the probe to both ends of the gas circuit in a gastight manner, the drying means being disposed in one of the gas lines, the lowermost end of one of the gas lines in the probe being sealed in a moisture-tight manner by a first seal which is opened when the probe is immersed in the metal bath and an uppermost end of one of said gas lines in the probe being sealed in a moisture-tight manner by a second seal which is opened by coupling the parts of the quick-connection coupling to each other.

44. The apparatus of claim 43, wherein the first and second seals seal said gas supply line of the probe.

45. A throwaway probe for measuring a gas content, in particular a hydrogen content, of a bath of liquid metal with a low partial pressure of oxygen, said probe comprising a gas supply line having an uppermost and a lowermost end which debouches at an end of the probe, a gas removal line having an uppermost and a lowermost end for collecting a gas which flows out of the gas supply line, said lowermost end of said gas removal being positioned proximate the lowermost end of the gas supply line, and drying means positioned within one of the gas lines for drying said gas, one of said gas lines being closed at both ends in a moisture-tight manner by breakable seals.

46. The throwaway probe of claim 45, wherein the gas line containing the drying means is closed at its lowermost end by a fusible stopper which melts at the temperature of the liquid metal.

47. The throwaway probe of claim 45, wherein the gas line containing the drying means is closed at its uppermost end by an elastic stopper, said elastic stopper being piercable by a hollow needle.

* * * * *